(12) United States Patent
Tennican et al.

(10) Patent No.: US 9,039,967 B2
(45) Date of Patent: May 26, 2015

(54) ANTISEPTIC APPLICATORS AND PACKAGING TECHNIQUES

(71) Applicant: Hyprotek, Inc., Spokane, WA (US)

(72) Inventors: Patrick O. Tennican, Spokane, WA (US); L. Myles Phipps, Shelton, WA (US)

(73) Assignee: Hyprotek, Inc., Spokane, WA (US)

( * ) Notice: Subject to any disclaimer, the term of this patent is extended or adjusted under 35 U.S.C. 154(b) by 106 days.

(21) Appl. No.: 13/757,318

(22) Filed: Feb. 1, 2013

(65) Prior Publication Data

US 2013/0202483 A1     Aug. 8, 2013

Related U.S. Application Data

(60) Provisional application No. 61/595,635, filed on Feb. 6, 2012.

(51) Int. Cl.

| | |
|---|---|
| *A61L 2/00* | (2006.01) |
| *B65B 41/18* | (2006.01) |
| *B08B 7/00* | (2006.01) |
| *A61F 13/15* | (2006.01) |
| *B65D 25/14* | (2006.01) |
| *A61B 19/02* | (2006.01) |
| *B65B 5/00* | (2006.01) |
| *B05C 1/00* | (2006.01) |
| *A61F 13/40* | (2006.01) |

(Continued)

(52) U.S. Cl.
CPC ................ *A61B 19/0256* (2013.01); *B65B 5/00* (2013.01); *B05C 1/00* (2013.01); *A61M 35/006* (2013.01); *B65D 75/40* (2013.01); *A61F 13/0253* (2013.01); *A61F 15/004* (2013.01); *A61F 15/005* (2013.01); *A61F 13/00063* (2013.01)

(58) Field of Classification Search
CPC ............. A61J 3/00; A61L 15/00; A61L 15/16
USPC ........... 422/28, 292; 53/449, 170, 558; 134/6, 134/22.1; 604/393; 220/495.01
See application file for complete search history.

(56) References Cited

U.S. PATENT DOCUMENTS

| | | | |
|---|---|---|---|
| 4,291,697 | A | 9/1981 | Georgevich |
| 5,438,984 | A | 8/1995 | Schoendorfer |

(Continued)

FOREIGN PATENT DOCUMENTS

| | | |
|---|---|---|
| CN | 2546003 | 4/2003 |
| CN | 2705167 | 6/2005 |

(Continued)

OTHER PUBLICATIONS

The PCT Search report mailed May 31, 2013 for PCT application No. PCT/US13/24649, 14 pages.

(Continued)

*Primary Examiner* — Monzer R Chorbaji
(74) *Attorney, Agent, or Firm* — Lee & Hayes, PLLC

(57) ABSTRACT

This disclosure describes example antiseptic applicators that may be used in combination with one or more cleansing, antimicrobial and/or antiseptic agents to reduce or eliminate contaminates on a surface. According to some embodiments, the disclosure describes that the applicators may contain an impermeable layer and a permeable layer, where the impermeable layer prevents contaminates for transferring from a user's hand to the permeable layer and the surface.

19 Claims, 4 Drawing Sheets

(51) Int. Cl.
  *B65D 75/40* (2006.01)
  *A61F 13/02* (2006.01)
  *A61F 15/00* (2006.01)
  *A61F 13/00* (2006.01)

(56) References Cited

U.S. PATENT DOCUMENTS

| | | | |
|---|---|---|---|
| 5,554,135 | A | 9/1996 | Menyhay |
| 5,556,375 | A | 9/1996 | Ewall |
| 5,637,080 | A | 6/1997 | Geng |
| 5,713,842 | A | 2/1998 | Kay |
| 5,730,530 | A | 3/1998 | Stoddard et al. |
| 5,732,716 | A | 3/1998 | Utecht |
| 5,973,221 | A | 10/1999 | Collyer et al. |
| 6,063,029 | A | 5/2000 | Saita et al. |
| 6,168,800 | B1 | 1/2001 | Dobos et al. |
| 7,282,186 | B2 | 10/2007 | Lake, Jr. et al. |
| 7,482,021 | B1 | 1/2009 | Tison et al. |
| 7,799,010 | B2 | 9/2010 | Tennican |
| 8,496,625 | B2 | 7/2013 | Brugger et al. |
| 2003/0007939 | A1 | 1/2003 | Murad |
| 2004/0037789 | A1 | 2/2004 | Moneuze et al. |
| 2004/0110841 | A1 | 6/2004 | Kite et al. |
| 2005/0084521 | A1 | 4/2005 | Hamada et al. |
| 2005/0129897 | A1 | 6/2005 | Zhou et al. |
| 2006/0142684 | A1 | 6/2006 | Shanbrom |
| 2007/0179373 | A1 | 8/2007 | Pronovost |
| 2008/0057136 | A1 | 3/2008 | Polyakov et al. |
| 2008/0119801 | A1 | 5/2008 | Moore |
| 2008/0181950 | A1 | 7/2008 | Bates et al. |
| 2009/0010998 | A1 | 1/2009 | Marchitto et al. |
| 2009/0012496 | A1 | 1/2009 | Tennican |
| 2009/0036541 | A1 | 2/2009 | Mardis |
| 2009/0324508 | A1 | 12/2009 | Bobbert |
| 2011/0052664 | A1 | 3/2011 | Tennican et al. |
| 2011/0184382 | A1* | 7/2011 | Cady ............................ 604/506 |
| 2011/0265834 | A1 | 11/2011 | Tennican |
| 2012/0288571 | A1 | 11/2012 | Tennican et al. |
| 2013/0287860 | A1 | 10/2013 | Tennican et al. |
| 2014/0243725 | A1 | 8/2014 | Tennican et al. |

FOREIGN PATENT DOCUMENTS

| | | | |
|---|---|---|---|
| CN | 1711845 | 12/2005 | |
| CN | 1813097 | 8/2006 | |
| EP | 1687039 | 1/2009 | |
| GB | 350384 | 6/1931 | |
| JP | 10110268 | 4/1998 | |
| JP | 2001525688 | 12/2001 | |
| JP | 2004049540 | 2/2004 | |
| JP | 2005511147 | 4/2005 | |
| JP | 2006503647 | 2/2006 | |
| JP | 2006526664 | 11/2006 | |
| JP | 2007536261 | 12/2007 | |
| WF | WO2005003436 | 1/2005 | |
| WF | WO2005089341 | 9/2005 | |
| WO | WO 85/03275 * | 8/1985 | ............. B65D 75/20 |
| WO | WO8503275 | 8/1985 | |
| WO | WO9204923 | 4/1992 | |
| WO | WO0156540 | 8/2001 | |
| WO | WO2004108091 | 12/2004 | |
| WO | WO2005025486 | 3/2005 | |
| WO | WO2006/089139 A2 | 8/2006 | |
| WO | WO2008009925 | 1/2008 | |
| WO | WO2009076718 | 6/2009 | |
| WO | WO2011163124 | 12/2011 | |

OTHER PUBLICATIONS

PCT Search Report mailed May 15, 2013 for PCT application No. PCT/US13/24635, 10 pages.
The PCT Search Report mailed May 13, 2013 for PCT application No. PCT/US13/24644, 10 pages.
Tjhe PCT Search Report mailed May 15, 2013 for PCT application No. PCT/US13/24651, 12 pages.
The Australian Office Action mailed Nov. 4, 2013 for Australian patent application No. 2010289415, a counterpart foreign application of U.S. Appl. No. 12/874,188, 3 pages.
The Australian Office Action mailed Mar. 13, 2014 for Australian patent application No. 2011207398, a counterpart foreign application of U.S. Appl. No. 13/554,962, 3 pages.
Translated Chinese Office Action mailed Oct. 17, 2013 for Chinese patent application No. 201180006632.3, a counterpart foreign application of U.S. Appl. No. 13/554,962, 13 page.
Translated Chinese Office Action mailed Apr. 10, 2014 for Chinese patent application No. 201180006632.3, a counterpart foreign application of U.S. Appl. No. 13/554,962, 19 pages.
Translated Chinese Office Action mailed Apr. 22, 2014 for Chinese patent application No. 201080047665.8, a counterpart foreign application of U.S. Appl. No. 12/874,188, 17 pages.
Translated Chinese Office Action mailed Aug. 12, 2013 for Chinese patent application No. 201080047665.8, a counterpart foreign application of U.S. Appl. No. 12/874,188, 13 pages.
The European Office Action mailed Sep. 12, 2014 for European patent application No. 11701925.7 a counterpart foreign application of US patent No. 8,846,008, 5 pages.
The European Search Report mailed Apr. 23, 2014 for European patent application No. , 11 pages.
Final Office Action for U.S. Appl. No. 13/554,962, mailed on Dec. 5, 2013, Patrick O. Tennican, "Antimicrobial Agents and Methods of Use", 14 pages.
Hospenthal et al., "Guidelines for the Prevention of Infections After Combat-Related Injuries", Journal of Trauma Injury, Infection, and Critical Care, vol. 64, No. 3, Mar. 2008, pp. 5211-5220.
Translated Japanese Office Action mailed Aug. 19, 2014 for Japanese patent application No. 2012-528071, a counterpart foreign application of US patent No. 8,778,387, 10 pages.
Japanese Patent No. JP6501857, which corresponds to International Patent Publication No. WO92/04923 already cited.
McGee et al., "Preventing Complications of Central Venous Catheterization", The New England Journal of Medicine, vol. 348, No. 12, Mar. 20, 2003, pp. 1123-1133.
The Mexican Office Action mailed Jul. 2, 2014 for Mexican patent application No. MX/a/2012/008482, a counterpart foreign application of U.S. Appl. No. 13/554,962, 2 pages.
The Mexican Office Action mailed May 26, 2014 for Mexican patent application No. MX/a/2012/002746, a counterpart foreign application of US patent No. 8,778,387, 4 pages.
Office Action for U.S. Appl. No. 13/924,410, mailed on Nov. 22, 2013, Patrick O. Tennican, "Antimicrobial Agents and Methods of Use", 15 pages.
Final Office Action for U.S. Appl. No. 12/874,188, mailed Dec. 19, 2012, Patrick O. Tennican et al., "Antimicrobial Medical Dressings and Protecting Wounds and Catheter Sites", 6 pages.
Non-Final Office Action for US Patent Application mailed on Feb. 15, 2013, Patrick O. Tennican et al., "Antimicrobial Agents and Methods of Use", 12 pages.
Non-Final Office Action for U.S. Appl. No. 12/874,188, mailed Feb. 7, 2014, Patrick O. Tennican et al., "Antimicrobial Medical Dressings and Protecting Wounds and Catheter Sites", 6 pages.
Office Action for U.S. Appl. No. 13/924,410, mailed on Mar. 28, 2014, Patrick O. Tennican, "Antimicrobial Agents and Methods of Use", 18 pages.
Non-Final Office Action for U.S. Appl. No. 12/874,188, mailed Jun. 29, 2012, Patrick O. Tennican et al., "Antimicrobial Medical Dressings and Protecting Wounds and Catheter Sites", 6 pages.
Office action for U.S. Appl. No. 12/874,188, mailed on Sep. 10, 2013, Tennican et al., "Antimicrobial Medical Dressings and Protecting Wounds and Catheter Sites", 6 pages.
Office action for U.S. Appl. No. 14/271,365, mailed on Sep. 11, 2014, Tennican et al., "Antimicrobial Medical Dressings and Protecting Wounds and Catheter Sites", 7 pages.
Office action for U.S. Appl. No. 13/757,423, mailed on Sep. 4, 2014, Tennican, "Adhesive Patch with Antimicrobial Composition ", 13 pages.
The PCT Search Report mailed May 20, 2011 for PCT Appliction No. PCT/US10/47756.

(56) References Cited

OTHER PUBLICATIONS

The PCT Search Report mailed Aug. 1, 2011 for PCT application No. PCT/US11/22150.

Singhal et al., "Wound Infection", eMedicine from WebMD <<http://www.emedicine,medscape.com>>, Updated Sep. 15, 2009, 32 pages.

"Versene Acid—Solubility", The Dow Chemical Company, Sep. 15, 2010, pp. 1-3.

"Versene NA Disodium EDTA Chelating Agent", The Dow Chemical Company, Oct. 2009, pp. 1-2.

Translated the Chinese Office Action mailed Oct. 23, 2014 for Chinese patent application No. 201080047665.8, a counterpart foreign application of US patent No. 8,778,387, 13 pages.

Translated the Chinese Office Action mailed Sep. 25, 2014 for Chinese patent application No. 201180006632.3, a counterpart foreign application of U.S. Appl. No. 13/554,962, 19 pages.

* cited by examiner

ANTISEPTIC APPLICATORS AND PACKAGING TECHNIQUES

CROSS REFERENCE TO RELATED APPLICATION

This claims priority to U.S. Provisional Patent Application No. 61/595,635 filed on Feb. 6, 2012 entitled "Antiseptic Applicators and Protective Devices," which is hereby incorporated by reference in its entirety.

BACKGROUND

Healthcare acquired infection (HAI) has been recognized as a significant cause of preventable mortality and morbidity. In the United States, HAI annually costs nearly 99,000 lives and billions of dollars in additional treatment and hospitalization. Klevens, et al., *Estimating Health Care-Associated Infection and Deaths in U.S. Hospitals*, 2002, Public Health Reports, Vol. 122, p. 160, 2007. Contamination of intravascular catheters, surgical sites and invasive procedure sites, frequently leads to device removal and replacement, prolonged parenteral antimicrobial therapy, and extended hospitalizations and rehabilitation.

The spread of multi-antimicrobial resistant organisms frequently are spread by healthcare providers' hands or medical equipment, from one colonized or infected patient to other susceptible patients. Surgical site infections may result from inadequate antiseptic preparations of the skin. Widespread use of chlorhexidine gluconate (CHG) for routine washing and wiping of pre-operative sites, has led to the increased incidence of resistant *Staphyloccus aureus*, both to methicillin (MRSA) and CHG, in some hospital environments.

BRIEF DESCRIPTION OF THE DRAWINGS

The detailed description is set forth with reference to the accompanying figures. In the figures, the left-most digit(s) of a reference number identifies the figure in which the reference number first appears. The use of the same reference numbers in different figures indicates similar or identical items or features.

DETAILED DESCRIPTION

Overview

Figure 1:
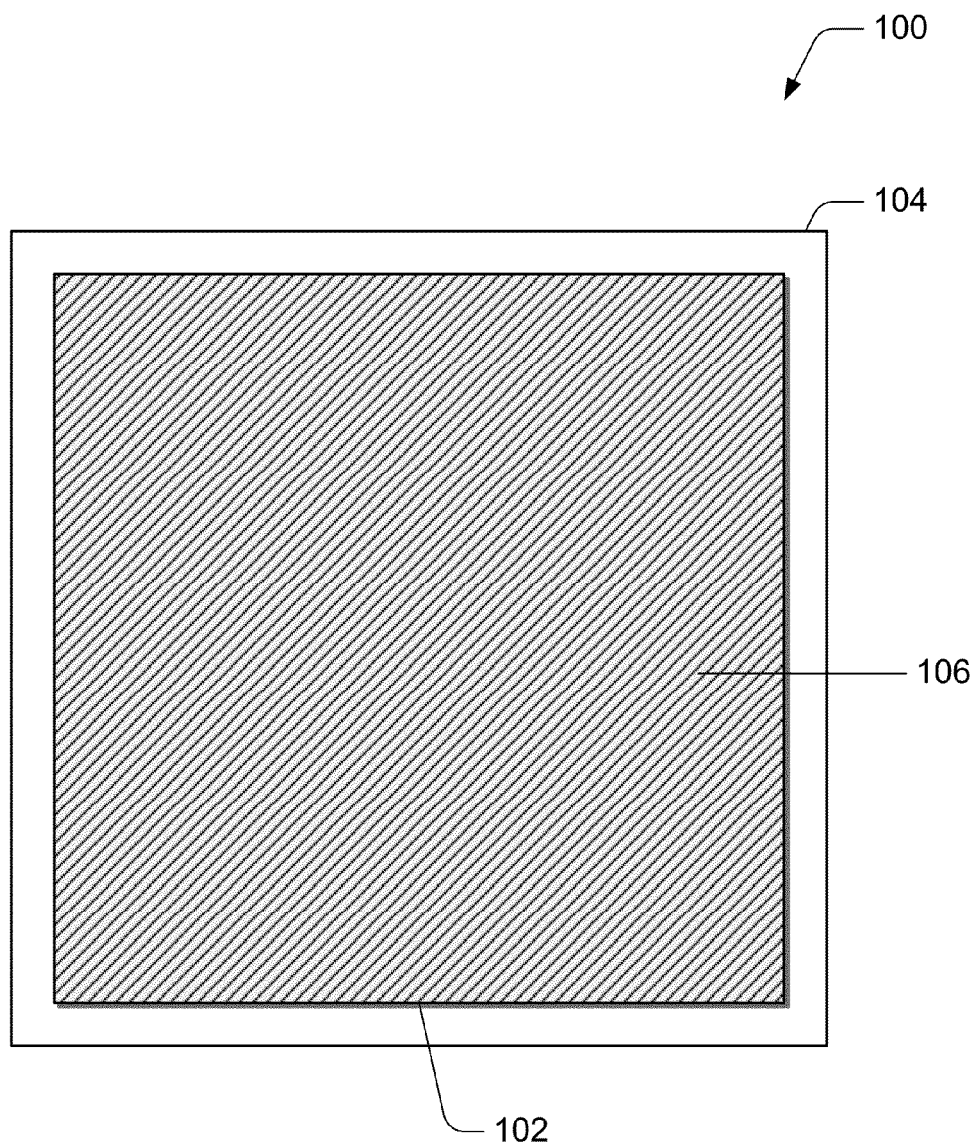
FIG. 1 illustrates an example antiseptic applicator which may include an impermeable layer and a permeable layer disposed with a cleansing, antimicrobial or antiseptic agent.

This disclosure describes medical applicators designed to reduce and/or prevent infections. In one embodiment, the disclosure describes example applicators or wipes that have an impermeable layer attached to a permeable, absorbent and/or adsorbent bottom layer. The sterile package of the applicators or wipes is designed to expose the impermeable layer to a user when opened and, therefore, prevents an existing infectious agent on the user hand from transferring to the permeable bottom layer and a patient or surface. In some embodiments, the applicators or wipes contain an antimicrobial composition that may be used alone or in combination with one or more cleansing, antimicrobial or antiseptic agent(s) to clean, sanitize and/or disinfect intravascular (IV) line ports, other IV components (e.g., syringes, lumens, valves, etc.), injection sites, blood draw sites (e.g., from a vein, artery, or capillary), medical equipment (e.g., digital thermometers or stethoscopes), wound sites, incision sites, peritoneal dialysis sites, drainage sites, or any other site or surface that is susceptible to infection.

In some embodiments, the disclosure describes an example applicator without an impermeable layer containing an antimicrobial or antiseptic agent comprising water, a low molecular weight alcohol, a peroxide or peroxide-generating agent and a chelating agent that is carried by permeable material. In this embodiment, the permeable material can be used as an applicator or wipe to clean, sanitize and/or disinfect much like a simple alcohol wipe would be used.

The detailed discussion below begins with a section entitled "Example Antimicrobial Composition", which describes in detail an example antimicrobial composition that may be included in the medical applicators and devices described herein. Next, the disclosure describes the "Example Antiseptic Applicator" followed by "Example Packaging of Antiseptic Applicator." Next, the disclosure describes an "Example Process" for operating an example antiseptic applicator. Finally, the disclosure concludes with a brief "Conclusion."

This overview, including section titles, is provided to introduce a selection of concepts in a simplified form that are further described below. The overview is provided for the reader's convenience and is not intended to limit the scope of the claims, nor the proceeding sections.

Example Antimicrobial Composition

In one example implementation, antimicrobial compositions that may be used in connection with the approaches described herein may include those described in, for example, International Patent Application No. PCT/US2011/022150, filed Jan. 21, 2011, to Tennican et al., and, U.S. Non-Provisional patent application Ser. No. 13/688,078, filed Nov. 28, 2012, to Tennican, which are incorporated herein by reference. For example, the antimicrobial compositions may include water ($H_2O$), a strong and non-toxic chelating agent such as ethylenediaminetetraacetic acid (EDTA)(e.g., disodium EDTA, calcium disodium EDTA, magnesium EDTA, potassium EDTA, gallium EDTA) or sodium citrate (or acids, salts, derivatives, or other forms of EDTA or sodium citrate), a short-chain monohydric alcohol (e.g., ethanol with a molecular formula of $C_2H_5OH$ and an empirical formula of $C_2H_6O$), and a strong, small molecule oxidizing agent such as hydrogen peroxide ($H_2O_2$). In one specific example, the compositions may consist essentially of water, EDTA, ethanol, and hydrogen peroxide. Additional ingredients can include thickeners, gellants, surfactants, foamers and/or foam stabilizers. However, in other examples, other antimicrobial compositions may be used in combination with the applicators and devices described in this disclosure.

The antimicrobial compositions may be in a liquid form or a gel form, and may be combined with one or more carriers or diluents, depending on the needs of a specific application. For example, if the antimicrobial composition is used as a cleaning agent the antimicrobial composition may be in a liquid form. In that case, the concentration of the various constituents may depend on, for example, a desired level of sanitation and/or disinfection, whether the composition is being applied directly to living tissue or to a medical device, and/or to avoid irritation of tissue to which the composition will be applied directly or indirectly (e.g., via a medical device to which the composition is or was applied).

In addition to providing disinfection at the time of the application, the antimicrobial compositions may also provide a lasting barrier against contamination. For example, even after volatile constituents of the composition (e.g., water, alcohol, hydrogen peroxide, etc.) have evaporated, the chelating agent may remain on the treated surfaces (e.g., multiple use vial or port cleaning/protecting device, stethoscope, fingers, surrounding tissue, etc.) as a barrier that will provide antibacterial, antifungal or sporicidal (e.g., preventing germination of the spores), anti-parasitic, spermicidal or spermiostatic (e.g., decrease the motility of spermatozoon) and antiviral qualities. By robbing the environment of components (e.g., iron, magnesium, and manganese) that are needed for the bacteria, spores, parasites, fungus and viruses to reproduce, the chelating agent provides a lasting defense to contamination even after other constituents of the antimicrobial composition have evaporated. Furthermore, the hydrogen peroxide in the antimicrobial compositions may induce a charge on a surface of materials (e.g., silicone materials) to which the antimicrobial compositions are applied, which make the materials more resistant to bacteria or other microorganisms.

The antimicrobial composition described above may also provide a visual indication of contamination when applied to a surface or material, such indication may allow users to identify and clean surfaces to prevent infection.

The term "about" or "approximate" as used in context of describing the example antimicrobial composition is to be construed to include a reasonable margin of error that would be acceptable and/or known in the art.

Example Applicator

Various medical applicators are described herein. Example antiseptic applicators are described generally with reference to FIGS. 1 and 2.

FIG. 1 shows an illustration of an example antiseptic applicator 100. The example antiseptic applicator includes an impermeable layer 102 coupled to a permeable, absorbent layer 104. The example antiseptic applicator 100 is shown as having a square shape, although alternative shapes are contemplated such as, for example, a round shape, a rectangular shape, an oval shape, a polygon shape, and the like. In some embodiments, impermeable layer 102 may be slightly smaller than the permeable layer 104, as shown in FIG. 1. However, in other embodiments, impermeable layer 102 may be larger than the permeable layer 104 or substantially the same size as the permeable layer 104. Example materials for the composition of the impermeable layer 102 include, but are not limited to, polyethylene, silicon oxide coated polymeric films, polypropylene, polysilicone, polytetrafluoroethylene, polyvinyl chloride, mylar, or mixtures thereof.

In some embodiments, the impermeable layer 102 may have a textured gripping surface 106. The textured gripping surface 106 on the impermeable layer 102 may include, but is not limited to, a ridged, coarse, bumpy, lined, dotted, reticulated texture or the like. The textured gripping surface 106 of the impermeable layer 102 may allow a user to grasp and use the antiseptic applicator minimizing the risk of the user's hand slipping off the applicator and contacting the surface to be cleaned, sanitized or disinfected.

In another embodiment, the impermeable layer may have a raised ridge (not shown) located around its periphery or edge. The raised ridge may be present in addition to or instead of the other textured embodiments described above. Furthermore, the ridge may be elevated from the interior surface of the impermeable layer sufficient to minimize the risk of the user's hand slipping off the applicator and contacting the surface to be cleaned, sanitized or disinfected.

In yet another embodiment, the impermeable layer 102 may prevent contaminates located on a user of the applicator (e.g., a user's hand) from transferring to the permeable layer 104 and, potentially, to the surface being cleaned, sanitized or disinfected. Additionally or alternatively, the impermeable layer 102 may prevent contaminates on a surface from transferring to the user of the applicator.

Figure 2:
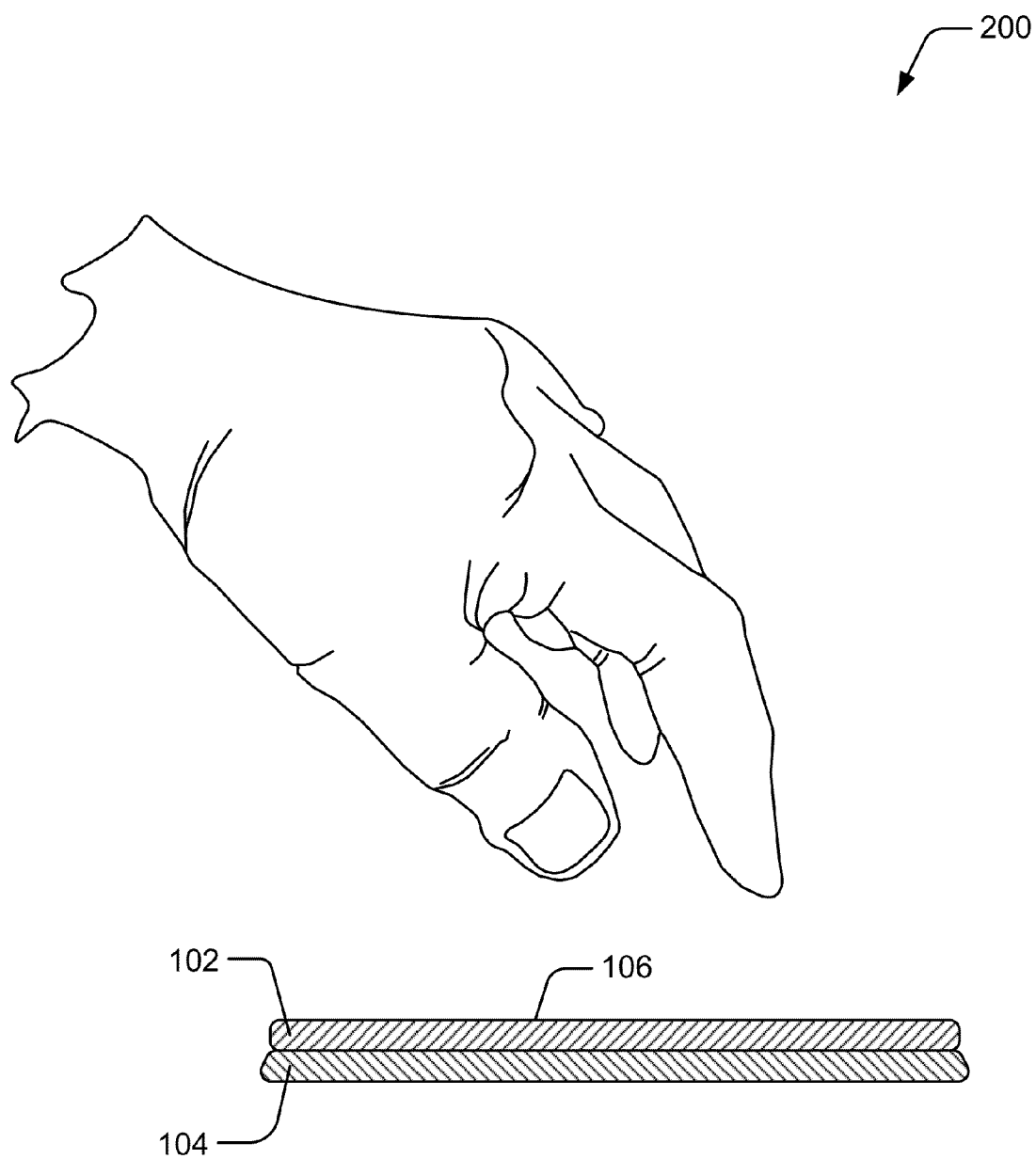
FIG. 2 illustrates an example environment where a user may grasp the impermeable layer of the example antiseptic applicator.

As shown in FIG. 1 and FIG. 2, the example antiseptic applicator 100 contains a permeable, absorbent and/or adsorbent layer 104 that would allow an antiseptic, antimicrobial or cleansing agent to be permeated throughout all or part of the layer. Example materials for the permeable layer 104 include, but are not limited to starch polymer, cellulosic gel, polyethylene foam, polyurethane foam, silicone open cell foam or mixtures thereof. Certain embodiments of the permeable layer 104 may include, but are not limited to, different surface treatments (e.g., siping, slitting, etc.), surface finishes (e.g., macro-, micro-, or nano-structures, etc.), contours (e.g., rounded, ribbed, protrusions, fingers, etc.) and/or combinations thereof to provide cleaning and/or scrubbing effectiveness.

In some embodiments, the permeable layer 104 contains a cleanser, including but not limited to, a surfactant, detergent or soap. In another embodiment, the permeable layer 104 contains a low molecular weight alcohol. In another embodiment, the permeable layer 104 contains peroxide or a peroxide-generating agent. In another embodiment, the permeable layer 104 contains a chelating agent. In another embodiment, the permeable layer 104 contains the example antimicrobial composition described in the preceding section. The example antiseptic applicator's permeable layer 104 is intended to come into contact with organic tissue, include but are not limited to, human or animal tissue. In another example, the permeable layer 104 is intended to come into contact with an inert material including, but not limited to, a medical device (e.g., thermometer, stethoscope, ultrasound equipment, otoscope, ophtalmoscope, electrocardiogram units, blood pressure monitors, scales or the like), a multiple use/dose vial, an intravascular (IV) line port, or another IV component.

In yet another embodiment, the example antiseptic applicator may be constructed without the impermeable layer 102. In this embodiment, the permeable layer 104 may contain the example antimicrobial composition described in the preceding section.

FIG. 2 shows an illustration 200 of a user's hand attempting to grasp the impermeable layer 102 of the example antiseptic applicator 100. The example antiseptic applicator 100 is shown from the side. In some embodiments, the user's gripping of the example antiseptic applicator 100 may be facilitated by the textured surface 106 of the impermeable layer 102.

Once the user grips the example antiseptic applicator 100, the user may use the applicator 100 to wipe or scrub an indentified surface, such as human tissue or a medical device. The impermeable layer 102 providing a nonslip surface 106 to aid the user's handling of the applicator and an impenetrable barrier to prevent contaminates from transferring from the user to the surface, or vice versa. In some embodiments, the user may receive a visual indication that the antimicrobial composition disposed within the permeable layer 104 has come into contact with one or more contaminants such as one or more bacteria, one or more spores, one or more parasites, one or more viruses, one or more bodily fluids, or mixtures thereof. The visual indication may be an indication of foaming or bubbling on the scrubbed or wiped surface.

Example Packaging of Antiseptic Applicator

Any of the various applicators described above may be sterilely packaged individually or in kits of multiple applicators in a variety of packages. Furthermore, the applicators themselves may additionally or alternatively be housed in a packaging that contains UV protective materials to inhibit breakdown of the cleansing, antimicrobial or antiseptic agents.

Figure 3A:
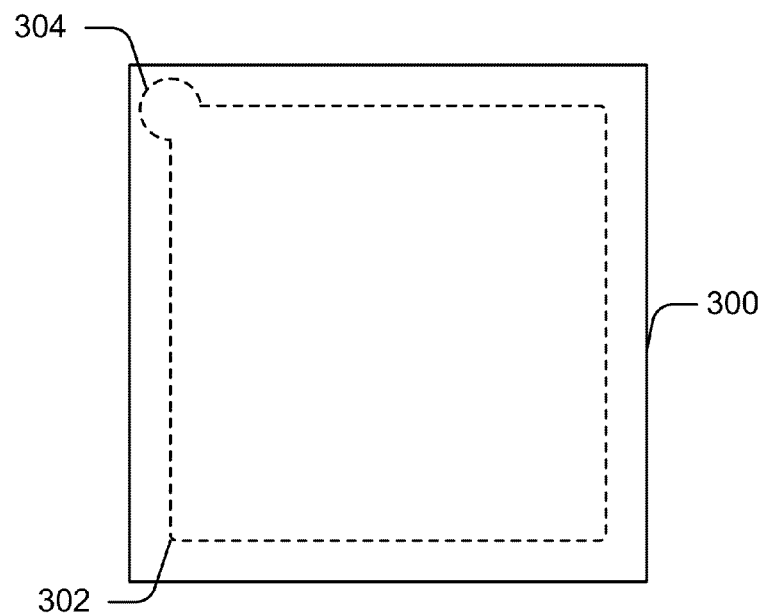
FIGS. 3A-3C illustrates various sterile packaging techniques for the example antiseptic applicators.

FIG. 3A shows an illustration of one embodiment of the sterile package 300 that may enclose the example antiseptic applicator 100. Each example antiseptic applicator may be individually sealed in a pouch or packet by sandwiching the example antiseptic applicator between multiple layers of thermoplastic material and sealing the sheets of material to each other around a periphery of the example antiseptic applicator by, for example, sonic welding, microwave welding, thermal bonding, or the like. In some embodiments, multiple example antiseptic applicators may be sealed in a pouch or packet as described above.

In some embodiments, the sterile package may contain a perforation or score line 302 and a tab 304 to facilitate opening of the sterile package 300. The user may pull back the tab 304 on the sterile package 300 following the perforation line 302 to expose the impermeable layer of the example antiseptic applicator to the user.

Figure 3B:
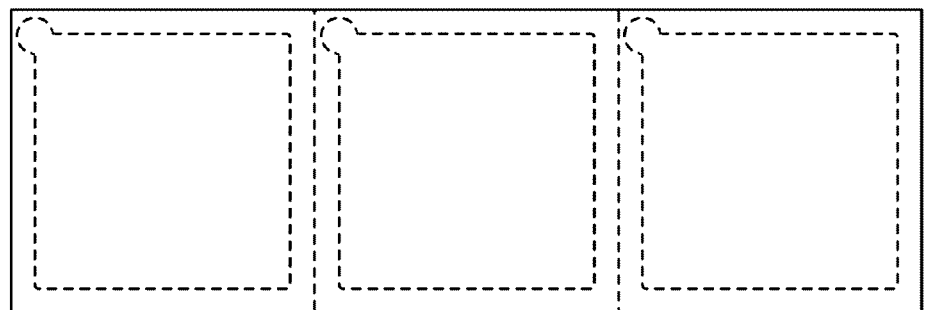

In certain embodiments, the sterile package 300 comprises, but is not limited to, a foil pouch, plastic lined pouch, foil lined pouch and/or a plastic tray. In one embodiment, multiple applicators may be packaged in a consecutive strip by placing the multiple applicators between sheets of thermoplastic material and then sealing the sheets of material to each other around the peripheries of each of the protective caps using any of the sealing methods described above. As illustrated by FIG. 3B, multiple applicators may be stored consecutively in a strip or series separated by perforation 306. In some embodiments, each of the packages in the consecutive strip may contain antiseptic applicators having the same cleansing, antimicrobial, or antiseptic agent. In other embodiments, each of the packages in the consecutive strip may contain antiseptic applicators having varying concentrations of the same cleansing, antimicrobial, or antiseptic agent. In yet other embodiments, each of the packages in the consecutive strip may contain antiseptic applicators having a different cleansing, antimicrobial, or antiseptic agent than an applicator stored in an adjacent package in the strip.

Figure 3C:
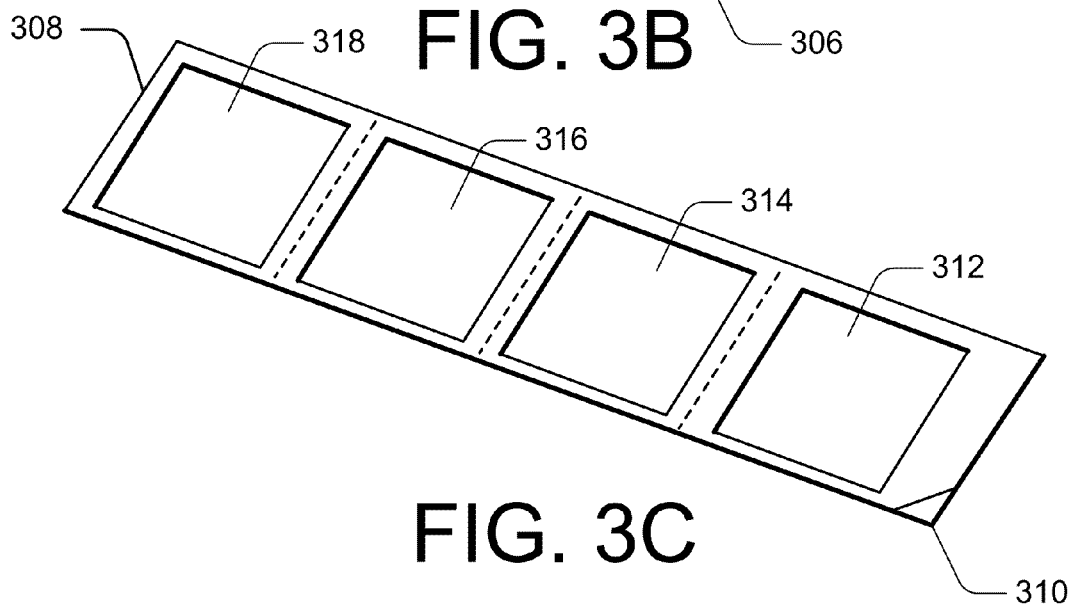

FIG. 3C illustrates another example sterile packaging to accommodate a specific multiple step medical procedure that requires a different cleansing, antimicrobial, or antiseptic agents or different concentration of the cleansing, antimicrobial, or antiseptic agents at different steps of the medical procedure. For example, a kit 308 may include a flap or projection 310 for exposing a first applicator 312 containing a cleansing agent to clean a desired site, a second applicator 314 containing a high concentration of an antiseptic agent to sanitize or disinfect the site, a third applicator 316 containing a lower concentration of the antiseptic agent, and a fourth applicator 318 containing an even lower concentration of the antiseptic agent to reduce the residual concentration of the antiseptic agent at the desired site. Kit 308 may comprise, but is not limited to, plastic lined pouch, foil lined pouch and/or a plastic tray. It should be understood that the applicators packed within kit 308 may contain any number of applicators containing any number of combinations of cleansing, antimicrobial, or antiseptic agents as described above with reference to FIG. 3B or to accommodate the steps of various medical procedures. In certain embodiments, kit 308 may also include at least one applicator that does not contain a cleansing, antimicrobial, or antiseptic agents.

Example Process

Figure 4:
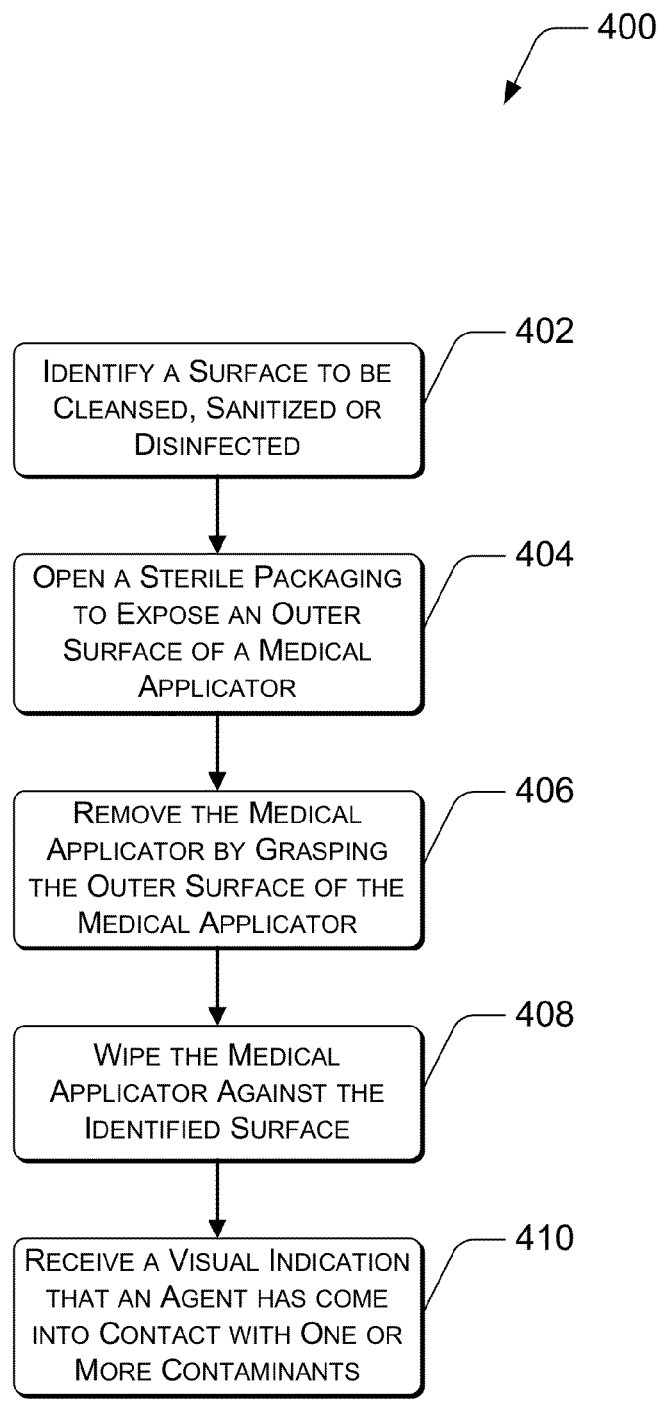
FIG. 4 is a flow diagram showing an example process for operating an example antiseptic applicator.

FIG. 4 illustrates an example process 400 for execution of the techniques described above of operating an example antiseptic applicator. The process 400 is illustrated as a logical flow graph. The order in which the operations are described is not intended to be construed as a limitation, and any number of the described operations can be combined in any order and/or in parallel to implement the process.

At operation 402, a surface to be cleansed, sanitized or disinfected may be identified. For example, a user may identify a surface such as human skin that needs to be sanitized prior to beginning a medical procedure.

At operation 404, a sterile package may be opened to expose an outer surface of a medical applicator. In the context of FIGS. 1 and 3A, the medical applicator may have an impermeable layer on the outer surface and the sterile package configured with a tab to open to the impermeable layer.

At operation 406, the medical applicator may be removed from the sterile packaging. For example, the medical applicator may be removed by grasping the impermeable layer on the outer surface of the medical applicator.

At operation 408, the medical applicator may be applied against the identified surface to be cleansed, sanitized or disinfected. For example, a permeable layer containing a cleansing, antiseptic, or antimicrobial agent of the medical applicator may by wiped, rubbed, dabbed, or otherwise moved over a portion of human skin.

Finally at operation 410, responsive to applying the applicator to the surface, a visual indication that the cleansing, antiseptic or antimicrobial agent may have come into contact with one or more one or more bacteria, one or more spores, one or more parasites, one or more viruses, one or more bodily fluids, or mixtures thereof may be received. For example, a visual indication such as bubbling or foaming may be present on the surface.

CONCLUSION

Although the disclosure describes embodiments having specific structural features and/or methodological acts, it is to be understood that the claims are not necessarily limited to the specific features or acts described. Rather, the specific features and acts are merely illustrative some embodiments that fall within the scope of the claims of the disclosure.

What is claimed is:

1. A medical applicator comprising:
   an impermeable layer, the impermeable layer having an outer surface;
   a permeable, absorbent layer having a top face coupled to the impermeable layer and a bottom face to interface with a surface;
   a cleansing, antimicrobial or antiseptic agent disposed within and carried by the permeable, absorbent layer; and
   a sterile package configured to expose the outer surface of the impermeable layer upon opening.

2. The medical applicator of claim 1, wherein the impermeable layer comprises polyethylene, silicon oxide coated polymeric films, polypropylene, polysilicone, polytetrafluoroethylene, polyvinyl chloride, mylar, or a mixture thereof.

3. The medical applicator of claim 2, wherein the outer surface of the impermeable layer has a ridged texture, a lined texture, a dotted texture, a reticulated texture or a combination thereof.

4. The medical applicator of claim 1, wherein the permeable, absorbent layer comprises starch polymer, cellulosic gel, polyethylene foam, polyurethane foam, silicone open cell foam, or mixtures thereof.

5. The medical applicator of claim 1, wherein the bottom face of the permeable, absorbent layer has a rough texture, a coarse texture, a smooth texture, a micro texture, a nano texture, or a combination thereof configured to scrub the material.

6. The medical applicator of claim 1, wherein the cleansing, antimicrobial or antiseptic agent comprises a surfactant, water, a low molecular weight alcohol, a peroxide or peroxide-generating agent or a chelating agent.

7. The medical applicator of claim 1, wherein the antimicrobial or antiseptic agent comprises:
   about 5 to about 50 mg/ml of ethylenediamine tetraacetic acid (EDTA);
   at most about 70% ethanol, by volume;
   at most about 7.5% hydrogen peroxide, by volume; and
   water.

8. The medical applicator of claim 1, further comprising sterile packaging to store the medical applicator, the packaging configured to expose the outer surface of the impermeable layer when opened.

9. The medical applicator of claim 8, wherein the sterile packaging is configured to store multiple medical applicators separately and consecutively in a strip, wherein each of the medical applicators is independently contained in the strip and may contain a same or a different cleansing, antimicrobial or antiseptic agent as an adjacent medical applicator in the strip.

10. The medical applicator of claim 8, wherein the sterile packaging is configured to store multiple medical applicators separately and consecutively in a series, wherein each medical applicator of the series contains no antimicrobial, or antiseptic agent or a specific cleansing, antimicrobial, or antiseptic agent to correspond to a specific step in a medical procedure and the packaging is further configured to open based on the steps in the medical procedure.

11. A method of preventing the spread of infectious agents comprising:
   identifying a surface to be sanitized or disinfected; and
   applying a medical applicator to the surface, the medical applicator comprising:
      an impermeable backing, the impermeable backing having an outer surface;
      a permeable face, the permeable face having a first layer coupled to the impermeable backing and a second layer configured to interface with the surface; and
      an antimicrobial or antiseptic agent disposed within the permeable face, the antimicrobial or antiseptic agent comprising:
         (a) water;
         (b) from about 20% to about 70% by volume of ethanol;
         (c) from about 0.5% to about 7.5% by volume of hydrogen peroxide; and
         (d) from about 5 mg/mL to about 50 mg/mL of ethylenediamine tetraacetic acid (EDTA), acids of EDTA, salts of EDTA, citrate, salts of citrate or any combination thereof.

12. The method of claim 11, wherein the surface to be sanitized or disinfected is an area of organic tissue or an area of an inert material.

13. The method of claim 11, wherein applying the medical applicator to the surface further comprises:
   opening a sterile packaging configured to expose the outer surface of the impermeable backing of the medical applicator;
   removing the medical applicator by grasping the outer surface of the impermeable backing of the medical applicator;
   wiping the second layer of the permeable face containing the cleansing, antimicrobial or antiseptic agent against the identified surface; and
   receiving, at least partly responsive to wiping, a visual indication that the cleansing, antimicrobial or antiseptic agent has come in contact with one or more bacteria, one or more spores, one or more parasites, one or more viruses, one or more bodily fluids, or mixtures thereof.

14. The method of claim 13, wherein the sterile packaging is configured to independently store multiple medical applicators where each of the medical applicators is stored consecutively in the strip and each of the medical applicators in the strip contain various concentration of the cleaning, antimicrobial or antiseptic agents.

15. The method of claim 13, wherein the outer surface of the impermeable backing is configured with a ridged, lined, dotted, tacky or reticulated texture.

16. A medical applicator comprising:
   a permeable, absorbent material, the permeable, absorbent material having an exterior base configured to interact with a surface;
   an antimicrobial or antiseptic agent disposed within the permeable, absorbent material, the antimicrobial or antiseptic agent comprising at least one or more of water, hydrogen peroxide, carbamide peroxide, ethylenediamine tetraacetic acid (EDTA), salts of EDTA, sodium citrate, or other biocompatible chelator, or alcohol; and
   a flexible, impervious material coupled to an exterior top of the permeable, absorbent material, the flexible, impervious material displayed when a sterile packaging is opened.

17. The medical applicator of claim 16, wherein the permeable, absorbent material comprises starch polymer, cellulosic gel, polyethylene foam, and/or silicone open cell foam.

18. The medical applicator of claim 16, wherein the antimicrobial or antiseptic agent comprises:
   about 5 to about 50 mg/ml of ethylenediamine tetraacetic acid (EDTA);
   at most about 70% ethanol, by volume;
   at most about 7.5% hydrogen peroxide, by volume; and
   water.

19. The medical applicator of claim 16, wherein the sterile packaging allows for multiple medical applicators to be stored separately and consecutively.

* * * * *